United States Patent [19]
Rueter et al.

[11] Patent Number: 5,849,938
[45] Date of Patent: Dec. 15, 1998

[54] SEPARATION OF METHANOL AND PROPYLENE OXIDE FROM A REACTION MIXTURE

[75] Inventors: Michael A. Rueter, Norristown; John C. Jubin, Jr., West Chester, both of Pa.

[73] Assignee: Arco Chemical Technology, L.P., Greenville, Del.

[21] Appl. No.: 926,420

[22] Filed: Sep. 2, 1997

[51] Int. Cl.⁶ .................................................. C07D 301/32
[52] U.S. Cl. .............................................................. 549/541
[58] Field of Search ............................................. 549/541

[56] References Cited

U.S. PATENT DOCUMENTS

| | | | |
|---|---|---|---|
| 3,881,996 | 5/1975 | Schmidt | 203/71 |
| 4,140,588 | 2/1979 | Schmidt | 203/92 |
| 4,584,063 | 4/1986 | Berg et al. | 203/51 |
| 4,597,834 | 7/1986 | Berg et al. | 203/51 |
| 4,620,901 | 11/1986 | Berg et al. | 203/51 |
| 4,824,976 | 4/1989 | Clerici et al. | 549/531 |
| 4,833,260 | 5/1989 | Neri et al. | 549/531 |
| 4,971,661 | 11/1990 | Meyer et al. | 203/54 |
| 5,000,825 | 3/1991 | Shih et al. | 203/3 |
| 5,523,426 | 6/1996 | Jubin, Jr. et al. | 549/531 |
| 5,591,875 | 1/1997 | Chang et al. | 549/531 |
| 5,621,122 | 4/1997 | Saxton et al. | 549/529 |
| 5,646,314 | 7/1997 | Croce et al. | 549/531 |

FOREIGN PATENT DOCUMENTS 0732327  9/1996  European Pat. Off. .

*Primary Examiner*—Ba K. Trinh
*Attorney, Agent, or Firm*—Stephen D. Harper

[57] ABSTRACT

Propylene is separated from the methanol present as a solvent in a crude olefin epoxidation product by means of an extractive distillation wherein a relatively heavy polar solvent having hydroxy groups such as water or propylene glycol is used as the extractive solvent. The method is also useful for removing water and impurities such as acetaldehyde from the propylene oxide.

18 Claims, 1 Drawing Sheet

SEPARATION OF METHANOL AND PROPYLENE OXIDE FROM A REACTION MIXTURE

FIELD OF THE INVENTION

This invention provides a method of recovering propylene oxide in purified form from an epoxidation reaction mixture which additionally contains methanol. Such mixtures may be formed by epoxidizing propylene with hydrogen peroxide using a titanium-containing zeolite as a catalyst and methanol as a reaction solvent. A hydroxy group-containing polar solvent such as water or propylene glycol is used as an extractive solvent in a distillation column so as to enhance the difference in volatility between propylene oxide and methanol, thereby permitting propylene oxide to be withdrawn as an overhead stream from the column. The extractive distillation may also be operated to reduce the level of other undesirable impurities such as water and acetaldehyde in the propylene oxide.

BACKGROUND OF THE INVENTION

In recent years, the production of propylene oxide from propylene using hydrogen peroxide as an oxidant and a titanium-containing zeolite as a catalyst has been proposed. Methanol is a particularly preferred reaction solvent for such purposes, as it tends to promote high catalyst activity and selectivity. Epoxidation processes of this type are described, for example, in U.S. Pat. Nos. 5,591,875, 4,833,260, 5,621,122, 5,646,314, and 4,824,976, EP Publ. No. 0732327, and Clerici et al. *J. Catalysis* 129, 159–167 (1991), the teachings of which are incorporated herein by reference in their entirety. Although such processes are capable of providing exceptionally high selectivity to propylene oxide, the crude reaction product thereby obtained typically contains only about 2 to 10 weight percent propylene oxide with the balance being predominantly methanol. However, propylene oxide and methanol normally have similar boiling points and thus can be difficult to separate quantitatively, especially where methanol is present in large excess. Minor quantities of certain by-products such as acetaldehyde are inevitably formed during epoxidation and subsequent processing. Since a satisfactory propylene oxide for commercial purposes should contain less than 100 ppm, and preferably less than 20 ppm, acetaldehyde, the development of methods for reducing the level of acetaldehyde by-product in such reaction mixtures is necessary. In addition, epoxidation processes of this type form water as a co-product, with the water being derived from the hydrogen peroxide oxidant. Depending upon the method used to generate the hydrogen peroxide to be used in the epoxidation, water may also be present in the feed to the reactor. While epoxidation processes catalyzed by titanium-containing zeolites are remarkably tolerant of water, it will be necessary for most commercial purposes to obtain propylene oxide in substantially anhydrous form. Thus, it is apparent that there is a need to develop purification methods capable of efficiently removing methanol, water and acetaldehyde simultaneously from a crude epoxidation reaction product when propylene oxide is present at a relatively low concentration.

SUMMARY OF THE INVENTION

We have now found that a crude epoxidation reaction product comprised of propylene oxide and methanol may be purified by the following process. The crude epoxidation reaction product is introduced into an intermediate section of an extractive distillation zone, while also introducing a polar solvent having a hydroxy functionality and a boiling point higher than that of methanol into an upper section of the extractive distillation zone. Propylene oxide is distilled overhead from said extractive distillation zone, with a bottoms stream comprised of methanol and the polar solvent withdrawn from a lower section. The process can be operated such that the water and at least a portion of the acetaldehyde present in the crude epoxidation reaction product are extracted into the polar solvent and removed in the bottoms stream.

DETAILED DESCRIPTION OF THE INVENTION

Figure 1:
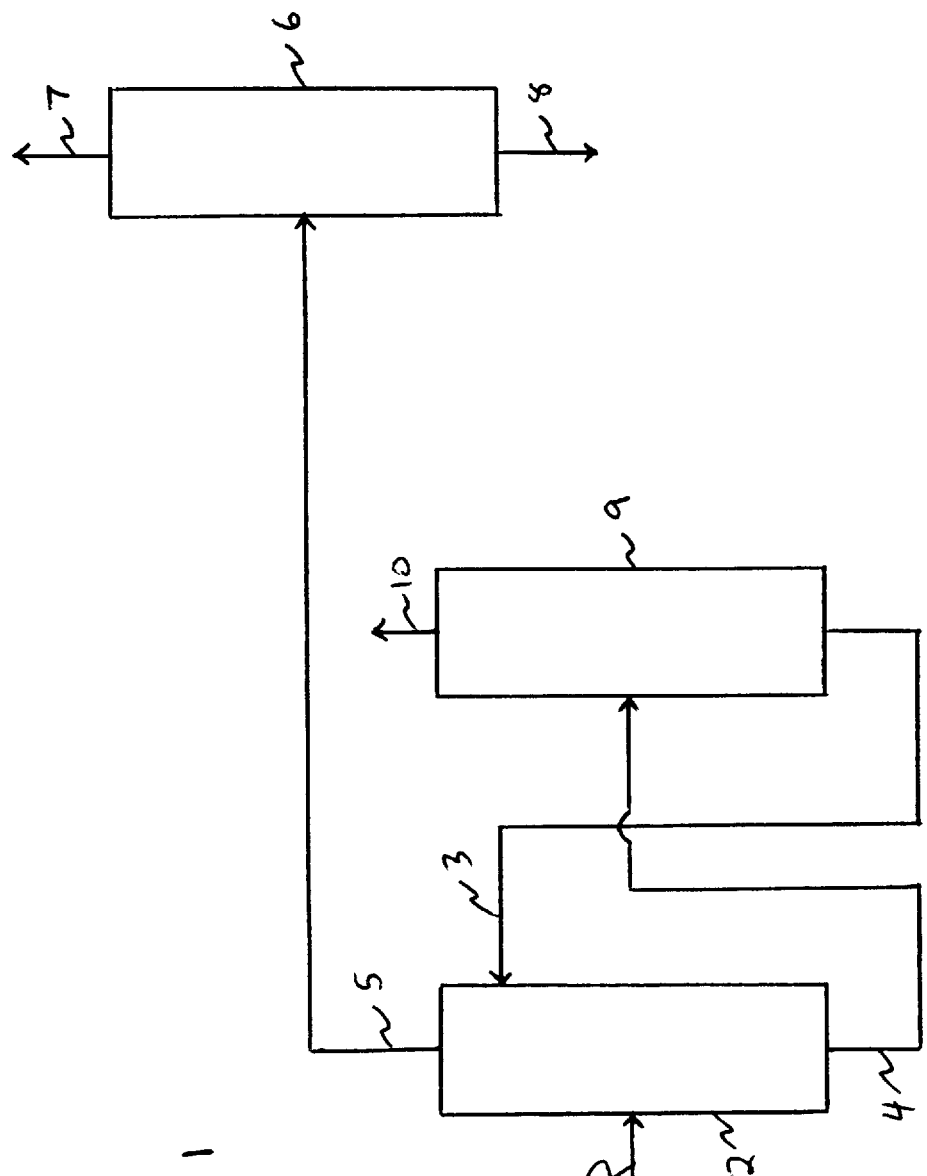
FIG. 1 to be explained in more detail hereafter, illustrates in schematic form an embodiment of the invention.

The crude epoxidation reaction product treated in accordance with the process of this invention is typically obtained by epoxidizing propylene with hydrogen peroxide or an equivalent thereof in a reaction medium where methanol is used as a solvent. Any unreacted propylene which may be present may be first largely or entirely removed by subjecting the crude epoxidation reaction product to an initial separation or fractionation using conventional distillation methods. For example, the propylene may be removed overhead using a flash drum or the like. The epoxidation catalyst, which may be, for example, a titanium-containing zeolite such as titanium silicalite, is preferably also separated by filtration or other such means from the crude epoxidation reaction product prior to processing in accordance with the present invention.

Depending upon the epoxidation conditions employed and the extent of propylene removal in the initial separation step, the crude epoxidation reaction product typically will have a composition comprised of the following components, in percent by weight:

propylene oxide 2–10
methanol 50–85
acetaldehyde 0.01–0.1
water 10–30
propylene glycol 0.1–20
other glycols and heavies 0–1
propylene and/or propane 0.01–0.1

The propylene glycol concentration range shown above includes the embodiment of the invention wherein propylene glycol is utilized as the polar solvent in the extractive distillation step and the propylene glycol recovered in the bottoms stream is incompletely separated from the methanol prior to recycling the methanol for use in epoxidation. Typically, the amount of propylene glycol actually generated as a by-product of epoxidation will represent less than 1 weight % of the crude epoxidation reaction product. If a glycol other than propylene glycol or another heavy component is utilized as the polar solvent in the aforedescribed embodiment, then the concentration of said polar solvent in the crude epoxidation reaction product will be higher than the range shown in the above table.

The extractive distillation is suitably carried out in any convenient distillation column or tower appropriate for the distillation of propylene oxide and methanol. For best results, the extractive distillation zone should contain at least 10 theoretical plates and ordinarily will contain 20 to 60 theoretical plates. The maximum number of theoretical plates is limited only by economic considerations. A single distillation column or tower is usually preferred for economic reasons, but the use of multiple distillation columns to accomplish the same result is not excluded.

The polar solvent to be supplied to the extractive distillation zone is a compound containing one or more hydroxy (—OH) functional groups and having a boiling point higher than that of methanol. In addition to water, suitable classes of polar solvents include, but are not limited to, glycols and glycol ethers. Glycols containing from 2 to 6 carbon atoms and oligomers thereof (e.g., dimers, trimers and tetramers) are generally suitable for use. Illustrative glycols include ethylene glycol, propylene glycol, diethylene glycol, dipropylene glycol, 1,4-butanediol, 2-methyl-1,3-propanediol, neopentyl glycol and the like and oligomers thereof. Illustrative glycol ethers include the $C_1$–$C_6$ alkyl ethers of propylene glycol, ethylene glycol and oligomers thereof such as di- and tripropylene glycol and di- and triethylene glycol. Mixtures of polar solvents (e.g., aqueous propylene glycol) could also be utilized. The amount of polar solvent supplied to the extractive distillation zone should be sufficient to achieve the desired degree of separation of methanol and other impurities such as acetaldehyde and water from the propylene oxide. This amount will vary, of course, depending upon a number of factors, including the identity of the polar solvent, but generally will be at least about 5%, based on the weight of the crude epoxidation reaction product. Typically, the polar solvent is fed to the extractive distillation zone at a rate (on a weight basis) which is from 5 to 35 percent of the feed rate of the crude epoxidation reaction product. Where propylene glycol is used as the extractive solvent, the amount of propylene glycol introduced is preferably 10 to 30 weight % of the crude epoxidation reaction product. The optimal amount will be dependent upon the propylene glycol concentration in the crude epoxidation reaction product (e.g., more propylene glycol in the reaction product will generally mean that less additional propylene glycol will need to be introduced and vice versa). The feed point for the polar solvent should be between the crude epoxidation reaction product feed point and the point at which the overhead stream comprising propylene oxide is withdrawn from the extractive distillation zone. This will help to minimize contamination of the propylene oxide by the polar solvent. Preferably, the polar solvent is introduced to the extractive distillation zone at a point not less than 2 theoretical plates below the overhead stream withdrawal point.

The point at which the crude epoxidation reaction product is introduced is an intermediate section of the extractive distillation zone, preferably from about 40% to 70% of the distance, in terms of theoretical plates, from the bottom to the top of the extractive distillation zone.

A suitable reflux/distillate ratio (molar) is important in achieving optimum results and generally will be in the range of from 5:1 to 15:1. The pressure under which the extractive distillation is operated is suitably around atmospheric pressure, e.g., from about 8 up to about 50 psia. The bottoms (reboiler) temperature will, of course, vary with the pressure but will typically be within the range of 90° C. to 120° C.

The extractive distillation conditions are selected so as to provide an overhead stream comprised predominately of propylene oxide. In a preferred embodiment, at least 95 weight % (more preferably at least 98 weight %) of the overhead stream is propylene oxide. The overhead stream will preferably contain less than 0.5 weight percent water (more preferably less than 0.05 weight percent water) and less than 1 weight percent methanol (more preferably, less than 0.2 weight percent methanol). The bottoms stream withdrawn from the extractive distillation will contain all or essentially all (i.e., 99+%) of the polar solvent (including any water present in the crude epoxidation reaction product) and a preponderance of the methanol (e.g., 99+%) originally present in the crude epoxidation reaction product. Depending upon the extractive distillation conditions selected, varying amounts of the acetaldehyde will be removed in the bottoms stream (e.g., 50 to 98%) while still achieving the desired separation of propylene oxide from methanol. For example, adjustments in reflux ratio, number of theoretical trays, overhead cut point and extractive solvent flow will change the acetaldehyde distribution.

In the accompanying drawing (FIG. 1) there is illustrated diagrammatically a representative system for carrying out the extractive distillation process of this invention. Thus, referring to the drawing, the reference numeral 1 designates the line for feeding the crude epoxidation reaction product to be treated to an extractive distillation zone 2. Heat may be supplied to the column or tower comprising the extractive distillation zone by means of a reboiler. A polar solvent is supplied as the extractive distillation solvent through line 3. The bottoms stream comprising methanol and other substances which are less volatile than propylene oxide under the extractive distillation conditions such as water and at least a portion of the acetaldehyde is withdrawn through line 4. The purified propylene oxide is removed in vapor form as an overhead stream via line 5. Further purification of the overhead stream may be performed. For example, if the overhead stream still contains unacceptably high levels of propane, propylene, acetaldehyde or other relatively light impurities, it may be introduced into an intermediate section of fractionator 6 and subjected to fractional distillation. The light impurities are withdrawn overhead through line 7, while a bottoms stream of repurified propylene oxide is withdrawn by way of line 8. An advantage of the present process is that fractionator 6 may be significantly reduced in size (and thus cost) as compared to the fractionator which would be required if the reaction mixture was directly subjected to fractional distillation rather than an initial extractive distillation. A further advantage is that fractionation of the acetaldehyde and propylene oxide is accomplished much more easily in the absence of methanol; the present process thus facilitates complete acetaldehyde removal by providing an overhead stream which is essentially free of methanol.

Subsequent to the removal of volatile components in fractionator 6, the propylene oxide obtained as a bottoms stream may, if so desired, be subjected to still further purification steps. For example, for many commercial applications the concentrations of impurities such as methanol, water and other low molecular weight oxygenates should be reduced to very low levels. This can be accomplished by any of the conventional methods known in the art such as, for instance, the extractive distillation procedures described in U.S. Pat. No. 5,000,825 (Shih et al).

The methanol in the bottoms stream may advantageously be recycled for use as the reaction solvent in an olefin epoxidation process, preferably after at least partial separation from the polar solvent by distillative means or the like. The separated polar solvent may likewise be recycled for further use in the present extractive distillation process. For example, the bottoms stream may be fed through line 4 to an intermediate section of fractionator 9 and subjected to fractional distillation. Methanol and other components of the bottoms stream which are more volatile than the polar solvent are removed overhead from fractionator 9 via line 10. The polar solvent recovered in the bottoms stream is returned to extractive distillation zone 2 through line 3. The extractive distillation process described in application Ser. No. 08/911,972, filed Aug. 15, 1997 (Attorney's Docket No. 01-2467A) may be utilized to remove at least a portion of any residual acetaldehyde from the methanol prior to its reuse in epoxidation if so desired.

While it is possible to completely separate the polar solvent from the methanol by distillation, it will often be economically advantageous to distill only a portion of the bottoms stream (with the remaining portion being fed directly back to the epoxidation reactor) since energy costs may thereby be reduced. The result will be that an appreciable amount of the polar solvent will be recycled to the epoxidation reactor together with the methanol. Ordinarily, however, this will not significantly affect the epoxidation results obtained since the polar solvents useful in the present purification process will be substantially inert under typical epoxidation conditions. It will, however, generally be desirable for the weight ratio of methanol to polar solvent in the epoxidation to be at least 2:1, more preferably at least 3:1.

EXAMPLES

Example 1

This example illustrates an embodiment of the process claimed herein wherein a crude epoxidation reaction product which has been subjected to an initial flash distillation to remove most of the unreacted propylene and which has the following composition is subjected to extractive distillation using propylene glycol as the polar solvent:

| Component | Wt. % |
|---|---|
| Propylene Oxide | 6.8 |
| Methanol | 61.3 |
| Water | 24.2 |
| Acetaldehyde | 0.039 |
| Propylene Glycol | 6.7 |
| Propylene & Propane | 0.055 |
| Other Heavy Components | 0.906 |

The crude epoxidation reaction product is fed to an extractive distillation tower containing 50 theoretical stages (including reboiler), the feed point being 19 stages from the top of the tower. Propylene glycol is fed to the 4th stage from the top of the tower at a flow rate which is 13.4% of the crude epoxidation reaction product flow rate on a weight basis. A purified propylene oxide product is taken as an overhead distillate. The propylene glycol extractive solvent is withdrawn from the bottom stage (reboiler), together with all, or nearly all, of the methanol and water as well as other relatively heavy components. The tower is operated at a reflux ratio (reflux-to-distillate) of 9. The pressure in the column condenser is set at 30 psia and the column operated with a pressure drop of 0.2 psi per tray, resulting in a bottom pressure of about 40 psia. The bottoms (reboiler) temperature is 104° C. and the top (condenser) temperature is 51° C.

Under these conditions, 99.8% of the propylene oxide in the crude epoxidation reaction product fed to the tower is recovered in the overhead distillate product and 99.995% of the methanol, 97.9% of the acetaldehyde, and all of the water are recovered in the bottom stream. The compositions of the product streams are as follows:

| Component | Distillate (wt. %) | Bottoms (wt. %) |
|---|---|---|
| Propylene Oxide | 99.6 | 0.014 |
| Methanol | 0.03 | 57.6 |
| Water | 0 | 22.7 |
| Acetaldehyde | 0.012 | 0.036 |
| Propylene Glycol | 0 | 18.8 |
| Propane & Propylene | 0.9 | 0 |
| Other Heavy Components | 0 | 0.85 |

Example 2

This example illustrates an alternative embodiment of the claimed process. A crude epoxidation reaction product which has been subjected to an initial flash distillation to remove most of the unreacted propylene and which has the following composition is subjected to extractive distillation using propylene glycol as the extractive solvent:

| Component | Wt. % |
|---|---|
| Propylene Oxide | 7.14 |
| Methanol | 50.8 |
| Water | 26 |
| Acetaldehyde | 0.0406 |
| Propylene Glycol | 15.1 |
| Propylene & Propane | 0.0576 |
| Other Heavy Components | 0.862 |

The crude epoxidation reaction product is fed to an extractive distillation tower containing 25 theoretical stages (including reboiler), the feed point being 13 stages from the top of the tower. Propylene glycol is fed to the third stage from the top at a flow rate which is 28% of the flow rate of the crude epoxidation reaction product feed on a weight basis. A purified propylene oxide product is taken as an overhead distillate. The propylene glycol extractive solvent is withdrawn from the bottom stage (reboiler), together with all or nearly all of the water and methanol as well as other components.

The tower is operated at a reflux ratio (reflux-to-distillate) of 9. The pressure in the column condenser is set at 30 psia and the column operated with a pressure drop of 0.2 psi per tray such that the bottom pressure is approximately 37 psia. Thus results in a bottoms (reboiler) temperature of 105° C. and a top (condenser) temperature of 51° C.

Under these conditions, 99.5% of the propylene oxide in the crude epoxidation reaction product fed to the column is recovered in the overhead distillate product and 99.98% of the methanol, 100% of the water and 89.5% of the acetaldehyde is recovered in the bottoms stream. The compositions of the product streams are as follows:

| Component | Distillate (wt. %) | Bottoms (wt. %) |
|---|---|---|
| Propylene Oxide | 98.84 | 0.63 |
| Methanol | 0.15 | 42 |
| Water | 0 | 21.5 |
| Acetaldehyde | 0.06 | 0.03 |
| Propylene Glycol | 0 | 35.7 |
| Propylene & Propane | 0.95 | 0 |
| Other Heavy Components | 0 | 0.74 |

We claim:

1. A method of purifying a crude epoxidation reaction product comprised of 2 to 10 weight percent of propylene oxide, 50 to 80 weight percent methanol and 10 to 30 weight percent water, said method comprising the steps of:

(a) introducing the crude epoxidation reaction product into an intermediate section of an extractive distillation zone;

(b) introducing a polar solvent having a hydroxy functionality and a boiling point higher than that of methanol into an upper section of said extractive distillation zone;

(c) distilling propylene oxide overhead from said extractive distillation zone; and (d) recovering a bottoms stream comprised of methanol and the polar solvent from a lower section of said extractive distillation zone.

2. The method of claim 1 wherein the polar solvent is selected from the group consisting of water, glycols, glycol ethers and mixtures thereof.

3. The method of claim 1 wherein the amount of the polar solvent introduced into the extractive distillation zone is at least 5 weight percent of the crude epoxidation reaction mixture.

4. The method of claim 1 wherein the crude epoxidation reaction product is additionally comprised of acetaldehyde.

5. The method of claim 4 wherein the amount of polar solvent is effective to render the acetaldehyde less volatile than propylene oxide and to cause at least a portion of the acetaldehyde to be removed as part of the bottoms stream.

6. The method of claim 1 wherein the intermediate section of the extractive distillation zone where the polar solvent is introduced is at least 2 theoretical plates below the point at which propylene oxide is withdrawn from the extractive distillation zone.

7. The method of claim 1 wherein the extractive distillation zone contains from 20 to 60 theoretical plates.

8. The method of claim 1 wherein the propylene oxide distilled overhead contains less than 0.5 weight percent water.

9. The method of claim 1 wherein the bottoms stream contains at least 99.9 percent of the methanol originally present in the crude epoxidation reaction product.

10. A method of purifying a crude epoxidation reaction product comprised of 2 to 10 weight percent propylene oxide, 50 to 85 weight percent methanol and 10 to 30 weight percent water, said method comprising the steps of:

(a) introducing the crude epoxidation reaction product into an intermediate section of an extractive distillation zone containing from 20 to 60 theoretical plates at a point which is from 40 to 70% of the distance in theoretical plates from the bottom to the top of the extractive distillation zone;

(b) introducing a polar solvent selected from the group consisting of water, glycols, glycol ethers and mixtures thereof into an upper section of said extractive distillation zone, in an amount which is at least 5 percent by weight of the crude epoxidation reaction product;

(c) distilling propylene oxide overhead from said extractive distillation zone, wherein the propylene oxide so distilled contains less than 0.05 weight percent water and less than 0.2 weight percent methanol; and (d) recovering a bottoms stream comprised of methanol and the polar solvent from a lower section of said extractive distillation zone.

11. The method of claim 10 wherein the polar solvent is propylene glycol.

12. The method of claim 10 wherein the crude epoxidation reaction product is additionally comprised of acetaldehyde.

13. The method of claim 12 wherein from 50 to 98 percent of the acetaldehyde in the crude epoxidation reaction product is removed as part of the bottoms stream.

14. The method of claim 10 wherein a reflux:distillate ratio of from 5:1 to 15:1 is utilized.

15. The method of claim 10 wherein the extractive distillation zone is operated at a pressure of from 8 to 50 psia and a bottoms temperature of from 90° C. to 120° C.

16. The method of claim 10 wherein the bottoms stream is subjected to fractional distillation wherein methanol is taken overhead and the polar solvent is recovered in a second bottoms stream.

17. The method of claim 16 wherein the methanol taken overhead is recycled for use in an olefin epoxidation process and the second bottoms stream is recycled for use in step (b).

18. The method of claim 10 wherein the crude epoxidation reaction product is formed by epoxidizing propylene with hydrogen peroxide using a titanium-containing zeolite as a catalyst and methanol as a reaction solvent.

* * * * *